(12) United States Patent
Nylund

(10) Patent No.: US 10,004,217 B2
(45) Date of Patent: Jun. 26, 2018

(54) LIGAMENT SUPPORT FOR HOOVES

(71) Applicant: SHINGS AB, Soderhamn (SE)

(72) Inventor: Marina Nylund, Kilafors (SE)

(73) Assignee: Shings AB, Soderhamn (SE)

( * ) Notice: Subject to any disclaimer, the term of this patent is extended or adjusted under 35 U.S.C. 154(b) by 351 days.

(21) Appl. No.: 14/429,788

(22) PCT Filed: May 27, 2013

(86) PCT No.: PCT/SE2013/050603
§ 371 (c)(1),
(2) Date: Mar. 20, 2015

(87) PCT Pub. No.: WO2014/051490
PCT Pub. Date: Apr. 3, 2014

(65) Prior Publication Data
US 2015/0238344 A1 Aug. 27, 2015

(30) Foreign Application Priority Data

Sep. 25, 2012 (SE) ........................ 1251086

(51) Int. Cl.
*A61F 5/01* (2006.01)
*A61D 9/00* (2006.01)
(Continued)

(52) U.S. Cl.
CPC .............. *A01L 3/00* (2013.01); *A01K 13/007* (2013.01); *A61D 9/00* (2013.01); *A61F 5/0111* (2013.01); *A61F 2005/0197* (2013.01)

(58) Field of Classification Search
CPC ...... A01L 1/00; A01L 1/04; A01L 3/00; A01L 3/02; A01L 3/04; A01L 3/06; A01L 5/00;
(Continued)

(56) References Cited

U.S. PATENT DOCUMENTS

| 115,311 A | 5/1871 | Halsey |
| 288,220 A | 11/1883 | Fennell |

(Continued)

FOREIGN PATENT DOCUMENTS

| EP | 1 449 497 B1 | 6/2007 | |
| GB | 190913708 A | 5/1910 | |
| GB | 2397483 A * | 7/2004 | ........... A01K 13/007 |

OTHER PUBLICATIONS

Poss, P. (n.d.). Hoof Anatomy and Bones of the Lower Leg. p. 1 "P2- middle phalanx". Retrieved Oct. 12, 2017, from http://www.ironfreehoof.com/hoof-anatomy-and-bones-of-the-lower-leg.html.*

(Continued)

*Primary Examiner* — Alireza Nia
*Assistant Examiner* — Rachel Berezik
(74) *Attorney, Agent, or Firm* — Dilworth & Barrese, LLP

(57) ABSTRACT

A ligament support for hooves, mountable on a hoof and in the mounted position effective for backing up the suspensory ligament between the hoof and the fetlock, comprising an elastic element the length of which is adapted to run via the rear of the pastern of the hoof, from an anchor point situated on the inside of the hoof to an anchor point situated on the outside of the hoof, and which, in an area located to the rear of the pastern, is coupled to an elastic cuff mountable around the leg.

10 Claims, 5 Drawing Sheets

(51) Int. Cl.
*A01K 13/00* (2006.01)
*A01L 3/00* (2006.01)

(58) Field of Classification Search
CPC ..... A01L 7/00; A01L 7/02; A01L 9/00; A01L 15/00; A01K 13/00; A01K 13/006; A01K 13/007; A61D 9/00; A43B 3/122; A61F 5/0111; A61F 5/05816; A61F 5/05841; A61F 2005/0197; A61F 13/04; A61F 13/064; A61F 5/0102; A61F 5/01; A61F 5/058; A61F 5/0585; A61F 13/043; A61F 13/066; A61F 13/08; A61F 13/085
See application file for complete search history.

(56) References Cited

U.S. PATENT DOCUMENTS

| | | | |
|---|---|---|---|
| 1,089,235 A | | 3/1914 | Levey |
| 4,444,269 A | | 4/1984 | Laurent |
| 5,115,627 A | * | 5/1992 | Scott ................ A01K 13/007 128/882 |
| 5,438,767 A | * | 8/1995 | Stein .................... A43B 3/12 36/11.5 |
| 6,192,989 B1 | | 2/2001 | Tooman |
| 6,560,951 B1 | | 5/2003 | Wood |
| 6,942,896 B1 | * | 9/2005 | Martin ................ A61F 13/4902 427/336 |
| 2003/0070403 A1 | | 4/2003 | Osha et al. |
| 2004/0255955 A1 | * | 12/2004 | Daly .................... A01K 13/007 128/869 |
| 2005/0066632 A1 | * | 3/2005 | Ford .................... A01K 13/007 54/82 |
| 2006/0064950 A1 | * | 3/2006 | Ford .................... A01K 13/007 54/82 |
| 2009/0288377 A1 | * | 11/2009 | Heid .................... A01K 13/007 54/82 |
| 2011/0000173 A1 | | 1/2011 | Lander |
| 2012/0089065 A1 | * | 4/2012 | Pflaster ................ A61B 5/1071 602/16 |

OTHER PUBLICATIONS

International Search Report, dated Dec. 11, 2013, from corresponding PCT application.

* cited by examiner

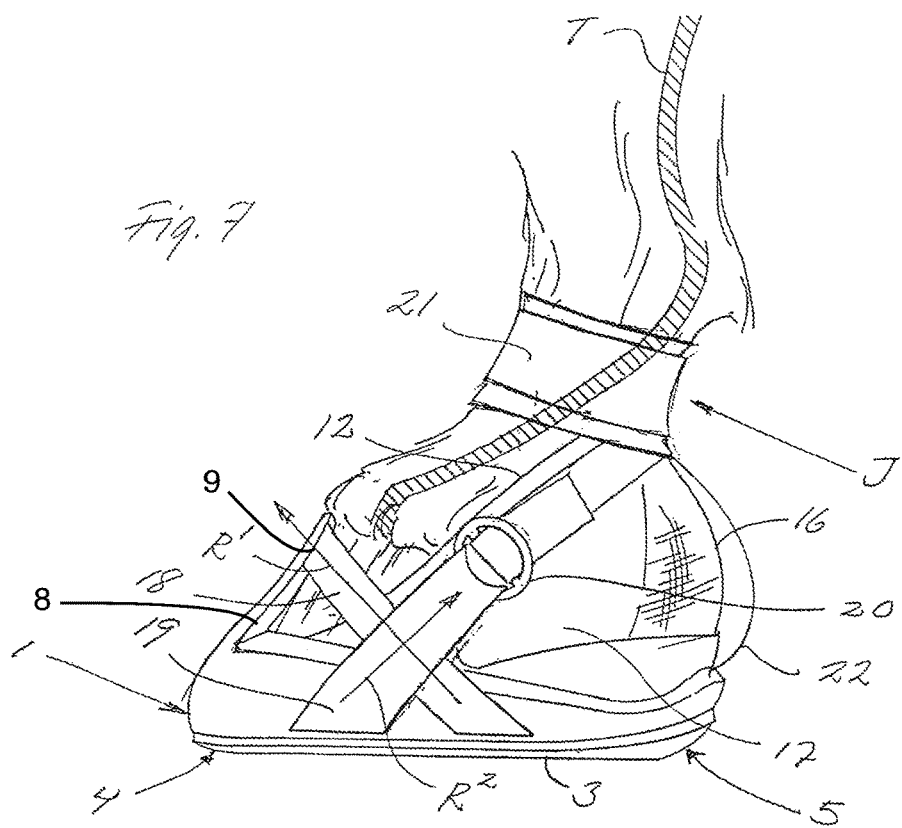

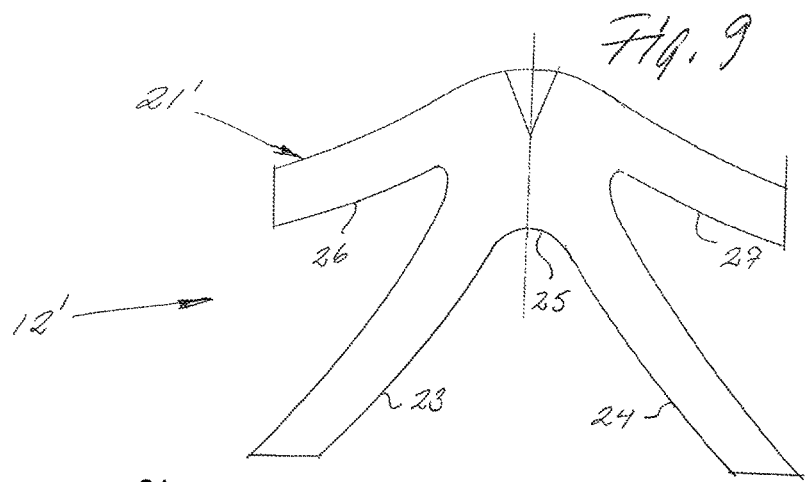
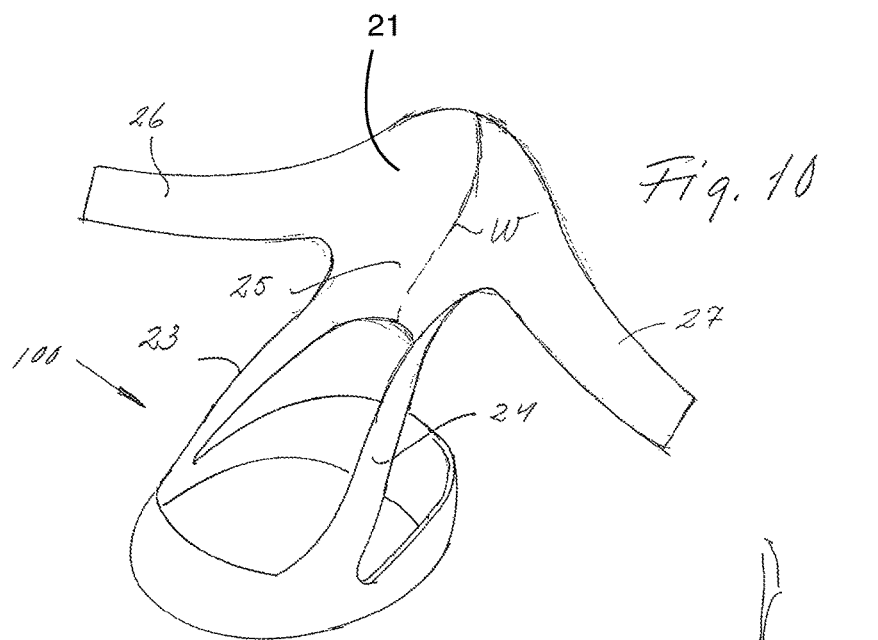
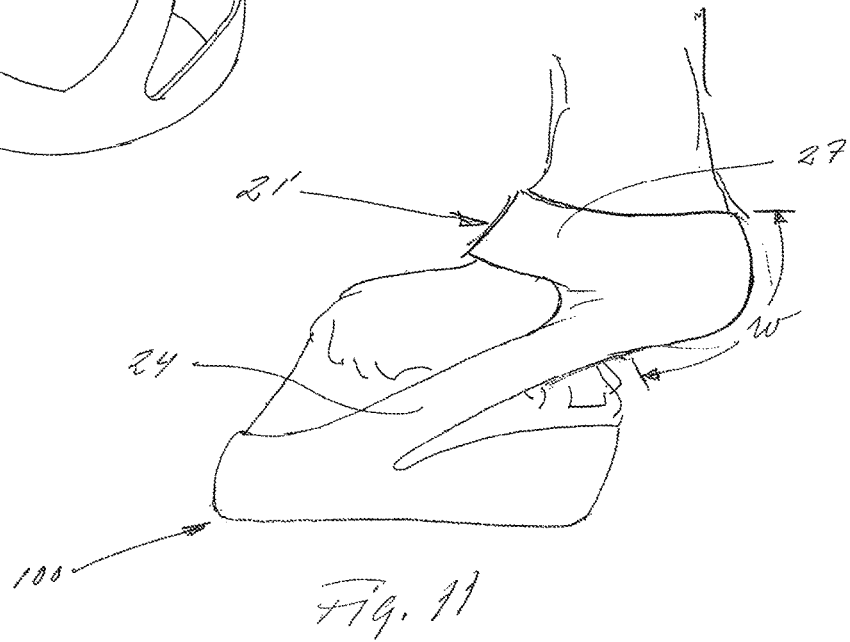

LIGAMENT SUPPORT FOR HOOVES

TECHNICAL FIELD OF THE INVENTION

The present invention relates to a support element for tendons of the lower part of the leg of horse and other hoofed animals. More specifically, the invention relates to a support element that is effective particularly to back up and relieve the pressure on the suspensory ligament, which from the back side branches off at the fetlock so as to, with an inner and outer, respectively, branching, run along the long pastern bone (first phalanx) and attach to a front part of the short pastern bone (second phalanx) and coffin or pedal bone (third phalanx) of the horse. In a further aspect of the invention, there is provided a ligament support for hooves adapted to be integrated in a boot for hooves or hoof boot for unshod hooves, and more precisely a non-metallic hoof boot that is attachable to a hoof without nails/horseshoe nails.

BACKGROUND AND PRIOR ART

The suspensory ligament is a centimeter thick structure that mostly consists of tendon tissue. In the forelimb, the suspensory ligament has its origin on the back side of the cannon bone (third metacarpal bone) immediately underneath the carpus, runs down along the cannon bone so as to, on a level with the fetlock of the horse, attach to the sesamoid bones of the fetlock and then branch off in lower lateral and medial branchings, which run on the respective side of the long pastern bone of the horse to be united in front to the long digital extensor tendon of the horse and attach on the dorsal side of the short pastern and coffin bone. The lower part of the suspensory ligament is the part that runs between the two lowermost attachments in the skeleton, from the proximal sesamoid bones and down to the final attachment in the short pastern/coffin bone. The purpose of the suspensory ligament is to carry and stabilize the fetlock and to work shock-absorbingly, and has to, in order to fulfil its purpose, be elastic. Upon loading of the fetlock, energy is stored in the suspensory ligament, which is released at the return of the fetlock from the loaded position.

A usual damage to the suspensory ligament is hyperextension, which regularly entails a long convalescence and healing time. Thus, there is a need of measures relieving the pressure on a damaged suspensory ligament and hastening the healing process.

A support for tendons and ligaments of horse is previously known from EP 1449497 B1. This device comprises a stiff upper collar shaped to surround the leg of the horse above the fetlock, and a stiff lower collar shaped to surround the leg underneath the fetlock. The collars are articulately connected via a swivel joint the axis of rotation of which should be arranged to coincide with the rotation of the fetlock. The object of the device is to limit the rotational ability of the fetlock. For this purpose, an elongate member is anchored in the two collars and arranged to extend between the collars on the back side of the leg. A central part of the solution is stated to be that said member should be non-elastic to its nature. The device is said to efficiently be able to replace tendons and ligaments and guarantee that all or essentially all downwardly directed force applied by the body mass during rest or training is transferred from tendons and ligaments to the front side of the leg.

It will be appreciated that the desired function imposes very high requirements of strength on the two collars and on the connection/joint between the collars, and that the material and construction costs therefore risk being high, as well as the weight of the device. It will also be appreciated that it is, in this solution, central that the collars and the connection joint always keep their exact location on the leg in order not for breaking forces to arise and counteract a natural movement in the fetlock/hoof.

SUMMARY OF THE INVENTION

Therefore, the invention aims at providing an alternative support to the suspensory ligament of the horse, which support is of low weight and does not rub against the leg of the horse and therefore is cautious to carry, as well as has a simple structure. The invention aims in addition at providing an easily mountable support that affords a resilient pressure-relief of the suspensory ligament of the horse.

One or more of said objects are met by a ligament support that is mountable on a hoof and in the mounted position is effective to back up/relieve the pressure on the suspensory ligament, comprising an elastic element the length of which is adapted to run via the rear of the pastern of the leg, from an anchor point situated on the inside of the hoof to an anchor point situated on the outside of the hoof, and which, in an area located to the rear of the pastern, is coupled to an elastic cuff mountable around the leg.

The elastic element is, with its one end, dimensioned to be fixed in an anchor point situated in a front area of the inside of the hoof and, with its other end, be fixed in an anchor point situated in a front area of the outside of the hoof.

The elastic element and the cuff may advantageously be formed integrally.

The cuff may be arranged for clasping the fetlock and extends for the purpose from an area underneath the fetlock to an area above the fetlock, in the mounted state of the ligament support.

The elastic element may be arranged to be detachably anchored in a conventionally formed horseshoe, for instance of plastic or metal, and more precisely in points of attachment that for the purpose are formed in opposite sides of a horseshoe.

The elastic element may alternatively be fixedly anchored in opposite sides of a sole included in a hoof boot that is attachable to a hoof without using nails/horseshoe nails.

The elastic element may alternatively be embedded in the sole of the hoof boot, and may alternatively be formed to be detachably anchored in the lower part/sole of the hoof boot.

In an alternative embodiment, the elastic element may be included in an inner boot connected with a sole. This inner boot may be co-cast with the sole in a double cast method.

The elastic element, as well as, where appropriate, also the hoof boot or inner boot integrated with the element, are preferably manufactured from synthetic material, from rubber, or from mixtures thereof.

In a second aspect of the invention, there is provided a ligament support integrated in a hoof boot, which is easy to mount and dismount, and which in the mounted position allows a natural hoof mechanism.

Said second aspect of the invention is met by the integration of the ligament support in a hoof boot of the type that is attachable to a hoof by means of two straps adjustable in their length, which hoof boot comprises:

a sole having an external ground contact surface the shape of which essentially corresponds to the shape of the underside of a hoof, and which extends in the longitudinal direction between a toe portion and a heel portion;

a first strap anchored in the sole and running from one side of the hoof boot to the other, across the front side of the hoof in the mounted position;

a second strap anchored in the sole and running from one side of the hoof boot to the other, above the back side of the hoof in the mounted position, in such a way that the first and second straps extend in directions intersecting each other on each side of the hoof boot, the second strap extending from the sole in such a direction that it is adapted to run on the back side of the leg above the hoof, and more precisely directed so that it, in the mounted position of the hoof boot on the hoof, runs at the rear of the pastern of the leg and which strap, on the back side of the hoof boot, is coupled to a cuff mountable around the leg, above the hoof.

By the present strap in the prescribed way being anchored in the sole to extend from the sole in a direction that permits and guides the strap to the prescribed high path around the leg above the hoof, the strap does not exert any surrounding pressure against the heel part and bulbs, and hereby neither the natural hoof mechanism is counteracted.

An additional result of the location of the second strap in the rear of the pastern is that the strap supports the contraction of the suspensory ligament upon raising of the joints after the hoof has been set down, when the suspensory ligament is stretched.

By strap, in the present text, a long narrow element should be understood having a cross-sectional profile that may be flat, quadrangular, round, or have another suitable geometrical shape. The strap has suitably certain elasticity in its longitudinal direction and may comprise an incorporated elastic section, but may alternatively in its entirety consist of an elastic material.

By the fact that the first/front strap and the second/rear strap extend in directions intersecting each other, and the points of intersection are situated above the sole in each side of the hoof boot, a distributed pressure from the sole against the underside of the hoof is produced. A load applied from the hoof to the front strap produces a resulting line of force toward the rear part or heel part of the sole. Correspondingly, a load applied by the hoof to the rear strap produces a resulting line of force directed toward the front part of the sole. The size of said lines of force is in direct proportion to the movement of the hoof in the hoof boot, whereby it can be avoided that unnecessary forces are applied to the hoof from the hoof boot. The straps co-operate alternately to counteract flopping about.

Advantageously, the second strap may be coupled on the back side of the hoof boot to a leash anchored in the heel portion of the sole. In this way, it is guaranteed that the hoof under no circumstances can step out of the hoof boot.

Preferably, at least said second strap is elastic in its longitudinal direction.

The first strap is embedded in the sole and runs unbroken through the sole, the part of the first strap embedded in the sole preferably comprising a respective strap portion, which is angled forward toward the toe portion of the sole.

A result of this embodiment is that the strap can be placed sufficiently far back in the sole, such as in the rear fourth of the sole, so as to, when the hoof is set down, be impinged on by the part of the hoof that carries the greatest instantaneous load, and to still connect to the sole in an area being frontal compared therewith, which results in that the strap leaves the heel part of the hoof free to expand, and allow a natural hoof mechanism.

Preferably, in the corresponding way, also the second strap is embedded in the sole to run unbroken through the sole, the part of the second strap embedded in the sole preferably comprising a respective strap portion, which is angled rearward toward the heel portion of the sole.

A result of this embodiment is that the strap can be placed sufficiently far forward in the sole, such as in the front fourth of the sole, so as to, upon take-off be impinged on by the part of the hoof that carries the greatest instantaneous load, and to still connect to the sole in an area being rear compared therewith, which results in that the strap can be brought to run essentially in the direction of the suspensory ligament, around the rear of the pastern.

In an advantageous embodiment, the first and second straps may be anchored to the sole in such a position that the geometrical point of intersection of said intersecting directions on the respective side of the hoof boot is situated right opposite or in front of, but never behind, an imaginary normal to the ground contact surface of the sole at a point situated on the longitudinal centre of the same.

The sole is made of an elastic material, such as plastic, rubber, or mixtures thereof, and has a circumferential, raised edge, which is arranged to, at rest, lean upturned against the outside of the hoof as well as when the hoof is set down, spring outward to absorb the lateral expansion of the hoof.

The sole typically has a rounded shape with an increasing width in the direction from the toe portion toward the heel portion, in correspondence to the underside of a hoof. By the sole, in the unloaded position, being formed so that it turns up around the outside of the hoof, the need is avoided of forming the sole with exaggerated width in the heel portion so as to, in this way, allow the hoof to expand laterally upon load, and thereby the play that such a design otherwise would cause is also avoided. More precisely, the sole adapts to the lateral expansion of the hoof upon loading by the raised edge being folded outward toward the sides, so as to, as soon as the load decreases, recapture its turned-up shape, thanks to the shape memory of the flexible material of the sole.

In one embodiment, the ability of the sole to alter its width may be enhanced by the raised edge of the sole, as seen in a cross-section through the sole, having a slightly concave shape in the unloaded position, in a rear area of the sole.

In a preferred embodiment, the sole is prepared for the fitting of studs, but may also alternatively comprise integrally formed studs.

In a preferred embodiment, the hoof boot according to the invention has an inner boot, which extends upward from the heel portion of the sole to the height of the rear of the pastern of the leg, and from this, its vertex, obliquely forward-downward on both sides of the hoof boot, toward the toe portion of the sole.

Said inner boot may be manufactured from a textile woven from synthetic thread, natural thread, or mixtures thereof, and its function is to protect the hoof and foremost the soft rear parts of the hoof by preventing that gravel, stone, and the like penetrate into the hoof boot.

The inner boot is open obliquely forward-upward and terminated forward by an element that is shaped as a loop and runs continually from one of the sides or outside of the hoof boot to the other side or inside of the hoof boot, essentially parallel to and inside said second strap, and accordingly via the rear of the pastern of the leg in the mounted position of the hoof boot.

The design of the forward/upward open inner boot facilitates the mounting of the hoof boot on the hoof, and the embodiment with an element shaped like a loop provides a stabilized edge around the opening of the inner boot, which contributes to the inner boot keeping its shape.

In a preferred embodiment, in its lower end connecting to the sole, said loop transforms into a border that runs projectingly over the edge of the sole from one side of the hoof boot to the other, via the heel portion of the sole. Correspondingly, in its lower end, the loop may transform into a wall that runs inside the edge of the sole from one side of the hoof boot to the other, via the toe portion of the sole.

Said loop, border, and wall are suitably manufactured from one and the same elastic material, such as plastic, rubber, or mixtures thereof, and may advantageously be cast integrally.

The inner boot is connected to the sole, such as by agglutination, vulcanization, or needlework. The inner boot and the sole may advantageously be interconnected by a double cast method.

In this way, said loop, border, and wall together form a frame to which the counter and side pieces are attached by either of agglutination, vulcanization, or needlework, for example. The coupling between said loop and side pieces may be made as a channel formed in the side piece through which the loop runs, from one side of the sole to the other. Said channel may be arranged to be coupled to the outer strap that is directed to run via the rear of the pastern, in the mounted position of the hoof boot on the hoof.

A part of the inner boot, which is limited by said loop and border, forms a counter that at least section-wise consists of an elastic material. A part of the inner boot, which is limited by said loop and border, forms side pieces that at least section-wise consist of an elastic material. The parts of the inner boot that herein are designated loop, border, and wall, or in other words the frame of the inner boot, consist typically of an elastic material having a higher shape stability than the material of the counter and side pieces, however still with a considerable ability to strain, preferably up to double the length in the unloaded state, without being permanently deformed.

The counter may have the special feature that it is designed with sections of different elasticity, alternatively has sections with elasticity acting in different ways/directions, which allows alternately acting strain and constriction. In doing so, parts of the counter contract at the same time as other parts are stretched out.

The rear central parts of the counter consist advantageously of a hard-wearing and tear-resistant elastic textile, while the parts connecting from the sides consist of an elastic such as rubber, elastomer, silicone, latex, or the like. In the different footfall phases of the horse, the shaping of the counter follows, by means of the alternately acting elastic sections, the natural movements of the hoof, whereby the counter obtains its unique qualities that, in addition to following the movements of the hoof, also significantly contribute to the exact form fit of the boot for the individual hoof. A good form fit prevents gravel and other particles from entering the hoof boot and causing discomfort to the horse. Moreover, a good form fit entails that sores can be avoided. The elastic material may also be utilized to obtain a holding function of the counter.

In a preferred embodiment, said counter comprises a loop formed for coupling the counter to the rear/second strap.

The elastic counter may be fixed around the long pastern bone of the horse by means of an elastic locking, such as a VELCRO™ tape, which prevents the counter from sliding down.

BRIEF DESCRIPTION OF THE DRAWINGS

The invention is explained below with reference to an embodiment example schematically shown in the appended drawings:

FIG. 7 shows the hoof boot mounted on a hoof at rest;
FIG. 8 shows the hoof boot mounted on a hoof loaded during a footfall;
FIG. 9 shows a ligament support;
FIG. 10 shows the ligament support in FIG. 9 integrated in a hoof boot,
and
FIG. 11 shows the ligament support in FIGS. 9 and 10 mounted on a hoof under load.

DETAILED DESCRIPTION OF PREFERRED EMBODIMENT EXAMPLES

Figure 1:
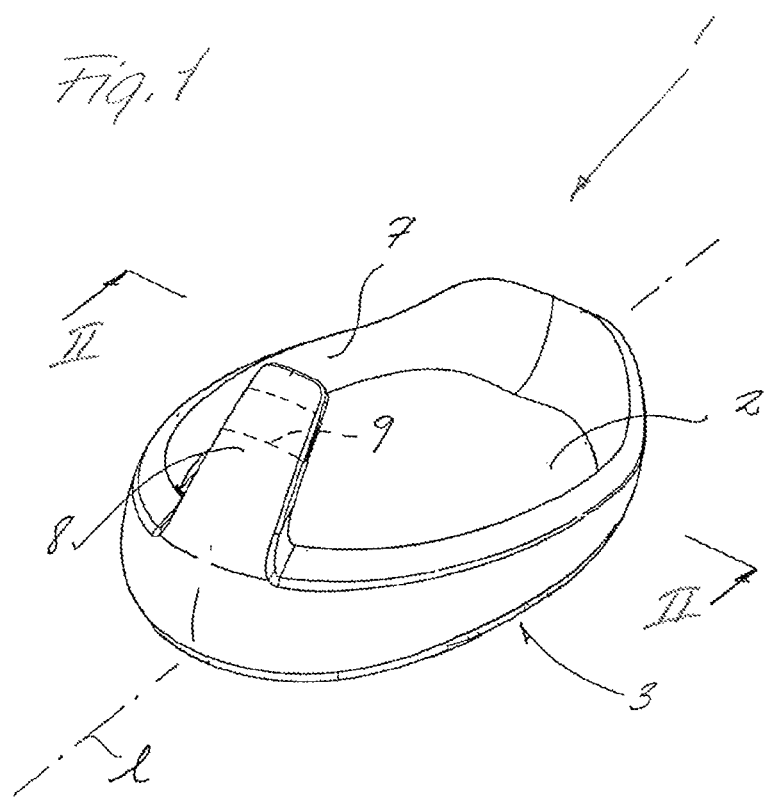
FIG. 1 shows a sole belonging to the hoof boot.
Figure 5:
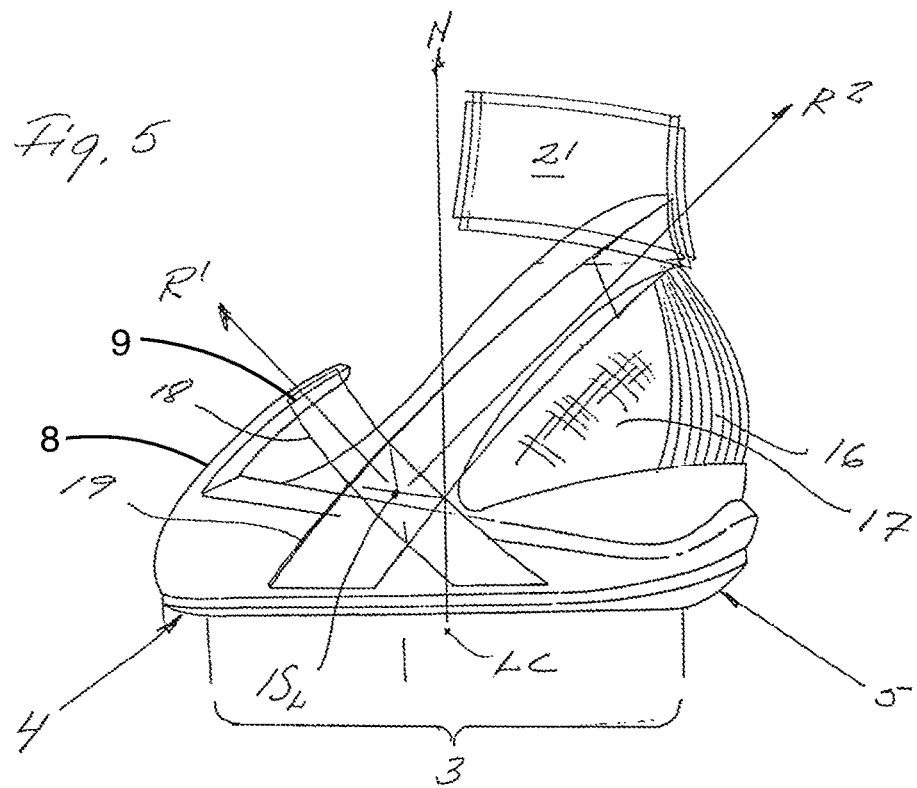
FIG. 5 shows the hoof boot in a phantom view.
Figure 6:
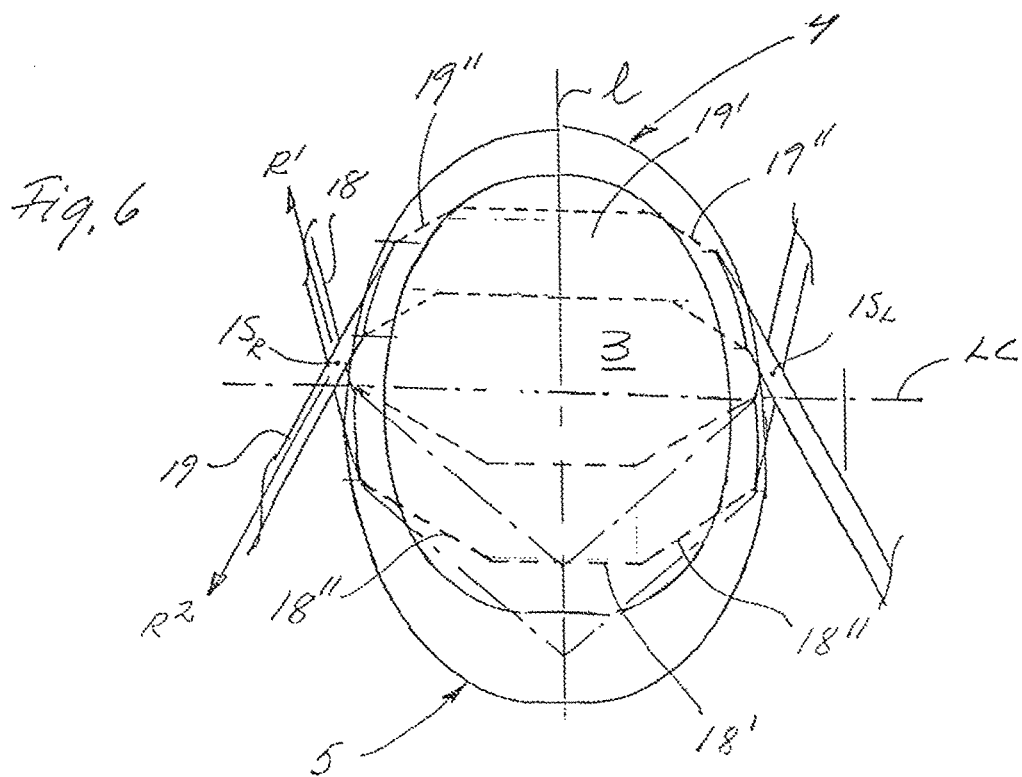
FIG. 6 shows the underside of the hoof boot.

FIG. 1 shows a sole 1 included in a hoof boot according to the invention. The sole 1 is cup-shaped and comprises a bottom 2 the shape of which essentially corresponds to the underside of a hoof, and the underside of which forms a ground contact surface 3. The ground contact surface 3 is best seen in FIG. 6. The bottom and ground contact surface of the sole extend in the longitudinal direction 1 of the hoof boot between a front toe portion 4 and a rear heel portion 5, see FIG. 5. A protruding edge 7 runs around the bottom of the sole, and has a tongue 8 in the toe portion having such a length that the tongue extends a good distance up along the capsule of the hoof in the mounted position of the hoof boot, as is best shown in FIGS. 7 and 8. A slot 9 is provided in the sides of the tongue 8 and extends through the tongue in ways illustrated by dashed lines in FIG. 1. The slot 9 is adapted for leading through a strap arranged and operative in the way described below. Said strap may alternatively be coupled to the tongue 8 in another arbitrary way.

Figure 2:
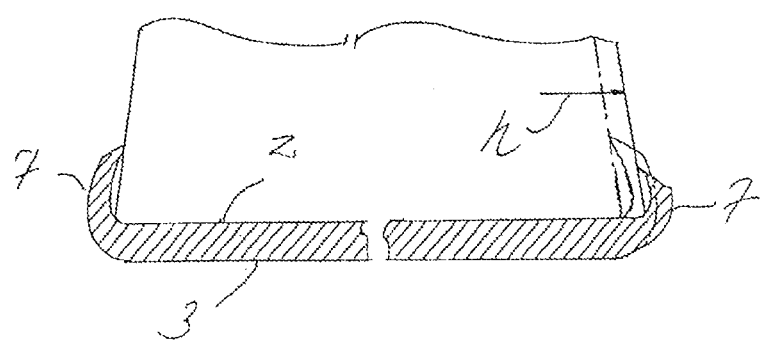
FIG. 2 shows a cross-section through the sole included in the hoof boot.

With reference to FIG. 2, it is shown how the protruding edge 7 abuts against the outside of the hoof both in the position of rest of the hoof (the left part of the drawing figure) and in the loaded position of the hoof (the right part of the drawing figure), in which the hoof has expanded laterally in the direction of the arrow h while running-out the edge 7, as a result of a natural hoof mechanism without hindrance.

Figure 3:
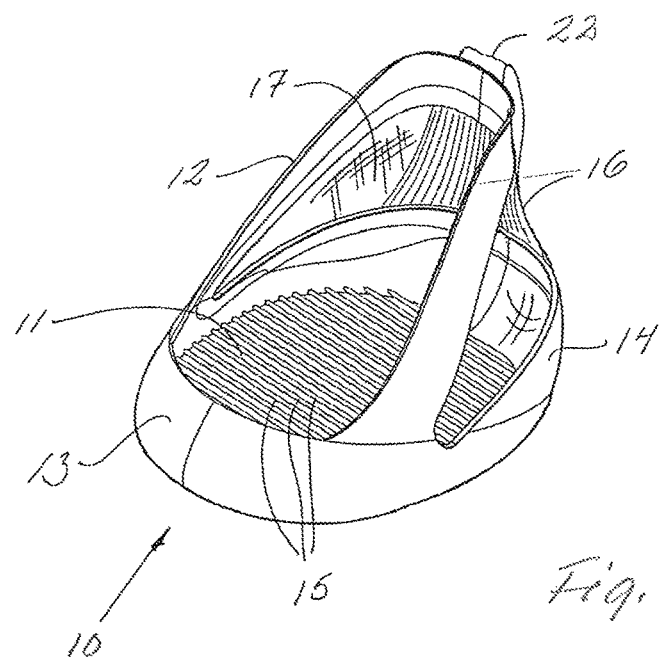
FIG. 3 shows an inner boot belonging to the hoof boot.

FIG. 3 shows an inner boot 10 adapted to be joined with the sole 1. The inner boot 10 is cup-shaped and comprises a bottom 11 from which a forward/upward open loop 12 rises. The loop 12, which mainly is strip-shaped, transforms forward into a wall 13, which runs around the toe portion of the inner boot and transforms rearward into a border 14, which runs around the heel portion of the inner boot. The inside of the bottom 11 of the inner boot is suitably made with a friction-enhancing surface, for example in the form of transverse ribs 15, which give a better hold for the hoof inside the inner boot 10. The embodiment with transverse ribs in the bottom of the inner boot contributes to enabling the hoof upon expansion to slide on the ribs laterally so that the edges of the sole are folded outward to absorb the lateral expansion of the hoof in a way that has been shown in FIG. 2. Hereby, it is prevented, for example, that the hoof "sucks fast" to the bottom of the inner boot.

The loop 12, the wall 13, and the border 14 form a frame included in the inner boot. In the frame, between the loop 12 and the border 14, there is carried an elastic counter 16 having side pieces 17, which are shaped to elastically surround the rear parts of the hoof in the mounted position of the hoof boot on the hoof, as is best seen in FIGS. 7 and 8.

The frame, comprising at least said loop 12, wall 13, and border 14, as well as the counter 16 and the side pieces 17 of the inner boot are elastic in the sense that they up to a certain expected load and strain return to their original shape. The elasticity may be inherent in the material, such as in the case of an elastic plastic, a rubber/synthetic rubber, or mixtures thereof.

The elasticity may alternatively or in addition be the result of a selected manufacturing method, such as a weaving technique, whereby the resulting fabric is afforded a non-locking stretchability. The stretchability and the elasticity may furthermore be different in different parts of the inner boot. Particularly, it is taught that the bottom 11 of the inner boot has a less flexibility and a greater resistance to strain than other parts of the inner boot.

Preferably, for the inner boot, and particularly in respect of the loop 12, a material is selected having toughness and ability to be elongated upon loading and store energy, and which, upon return from the loaded position, acts like a spring that engages the rear of the pastern and provides a back up to the suspensory ligament upon raising of the joint/leg in the final phase of the footfall.

In the light of the large variation in size and weight that different breeds of horse have, it is appreciated that the invention cannot be limited to a more closely specified elasticity and strain capacity of the different parts of the hoof boot. However, the inner boot should have such stretchability that it can be opened manually so as to allow insertion of a hoof into the hoof boot.

In the mounted position of a hoof, the counter 16 is stretched over the rear protrusion of the hoof in such a way that the elasticity of the elastic counter is utilized in the interval of 30 to 70% and most advantageously in the interval of 40 to 60% of maximum stretchability. From this, it is also appreciated that the counter has sufficient elasticity to allow a natural hoof mechanism. By the fact that the counter in this way seals around the rear protrusion, it is prevented that gravel and stones or other foreign materials penetrate in between the hoof boot and the hoof.

Figure 4:
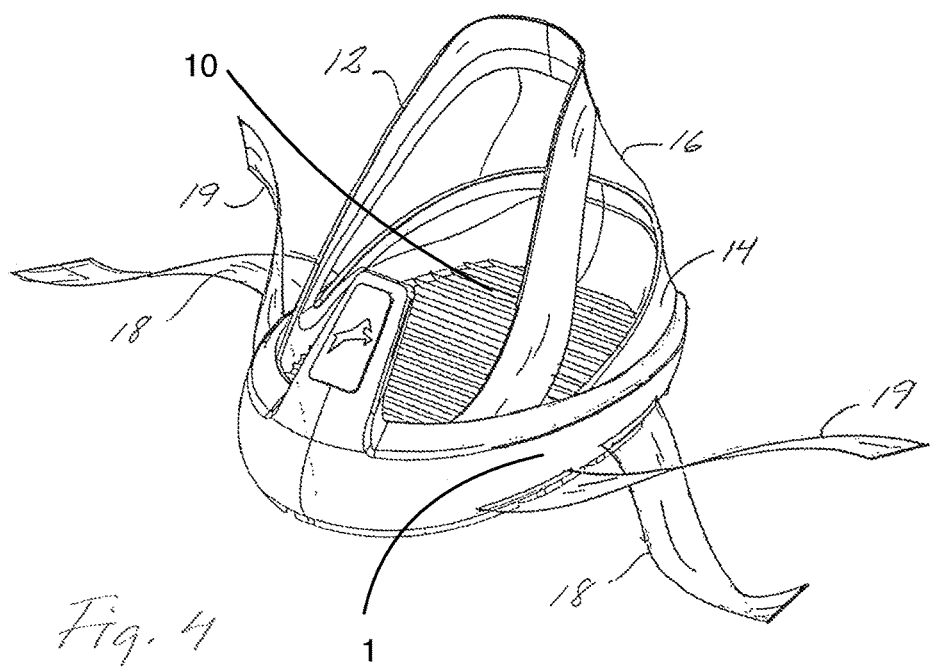
FIG. 4 shows the inner boot and the sole in a mutually mounted state.

FIG. 4 shows the inner boot 10 and the sole 1 in a mutually joined position. In FIG. 4, there are also illustrated a pair of straps 18 and 19 anchored in the sole, which are effective for the fastening of the hoof boot on a hoof in a way that is explained in more detail below.

With reference also to FIGS. 5, 6, 7, and 8, it will now be explained in more detail how said straps 18 and 19 are arranged. A first strap 18 is anchored in the sole to run, in the mounted position, from one side of the hoof boot to the other across the front side of the hoof. Said first strap 18 may also be designated a front strap. A second strap 19 is anchored in the sole to run, in the mounted position, from one side of the hoof boot to the other above the back side of the hoof. Said second strap 19 may also be designated a rear strap. The straps 18 and 19 extend in intersecting directions $R^1$ and $R^2$, which on each side of the hoof boot intersect each other in a respective geometrical point of intersection $IS_L$, $IS_R$.

The first or front strap 18 acts to prevent the movement of the hoof boot rearward in relation to the hoof, and the second or rear strap 19 acts to prevent the movement of the hoof boot forward in relation to the hoof. Thus, the front strap 18 and the rear strap 19 will be force-wise operative primarily upon loading during a footfall. More precisely, upon loading, said front strap 18 produces alternately a resulting line of force toward the rear part or heel portion 5 of the sole, while said rear strap 19 upon loading produces a resulting line of force directed toward the front part or toe portion 4 of the sole.

The first strap 18 starts out from the sole 1 in such a direction $R^1$ that it is adapted to, upon mounting, run high up on the capsule of the hoof, and according to the embodiment example more precisely through the slot 9 in the tongue 8. The strap 18 may be elastic in its longitudinal direction, and is tightenable and fixable by means of an expedient locking device (not shown). Alternatively, or in addition, the strap 18 may have a VELCRO™ tape for the tightening and fixation of the strap.

The second strap 19 starts out from the sole 1 in such a direction $R^2$ that it is adapted to, upon mounting, run above the hoof, and more precisely to run around the leg, via the rear of the pastern J of the leg. The strap 19 is elastic in its longitudinal direction, and is tightenable and fixable by means of an expedient locking device 20. Alternatively, or in addition, the strap 19 may have a VELCRO™ tape for the tightening and fixation of the strap.

The strap 19 is furthermore coupled to a cuff 21 that is attachable around the leg and tightenable and fixable by means of a locking device, not shown in detail, such as a VELCRO™ tape. The cuff 21 preferably consists of an inner layer of soft elastic material carried on the inside of a more stable outer layer, which can be tightened around the leg. The coupling between the strap 19 and the cuff 21 may in an advantageous embodiment be realised in the form of a channel running in the cuff and through which the strap 19 extends, movable in its longitudinal direction.

Said cuff 21 is suitably also connected with the inner boot 10, wherein the loop 12 of the inner boot in the area of its vertex, which is situated on the back side of the leg in the mounted position of the hoof boot, can be coupled to the cuff on the inside thereof to extend therefrom forward/downward toward the toe portion of the hoof boot. In doing so, the loop 12 is preferably fixedly anchored in the cuff 21 in the area where both run via the rear of the pastern at the back of the hoof and the leg.

A leash 22 co-operating with the strap 19 and/or with the cuff 21 may, where appropriate, be anchored in the hoof boot, for example in the heel portion of the sole, to efficiently guarantee that the hoof boot does not loosen, even when moving in extreme terrain.

The straps 18 and 19 are preferably anchored in the sole 1 in such a way that they run without interruption, i.e., continuously, through the sole from one side to the other. The straps may be fixed in the sole by embedment in connection with the casting of the sole.

As may be best seen in FIG. 6, the first strap 18 may have, in the sole 1, an intermediate strap portion 18', which extends transversely to the longitudinal direction of the sole, and which in each end, inside the side edges of the sole, connects to a respective strap portion 18'', which is angled forward toward the toe portion 4 of the sole.

Correspondingly, the second strap 19 may have, in the sole 1, an intermediate strap portion 19', which extends transversely to the longitudinal direction of the sole, and which in each end, inside the side edges of the sole, connects to a respective strap portion 19'', which is angled rearward toward the heel portion 5 of the sole.

Alternatively, the angled portions 18'' and 19'', respectively, of the first and/or second straps may meet in the middle of the sole without any interconnected transverse strap portion, essentially in the way illustrated in FIG. 6 by dash-dotted lines concerning the first strap 18.

By the measures described above, the directions R¹ and R² of the straps 18 and 19 starting out from the sole are determined. In a preferred embodiment of the hoof boot, the directions R¹ and R² are determined in such a way, see FIGS. 5 and 6, that their geometrical intersection points $IS_L$ and $IS_R$ on the respective side of the hoof boot are situated right opposite or in front of an imaginary normal N to the ground contact surface 3 of the sole at a point LC situated on the longitudinal centre of the same.

In its embodiment described above, the hoof boot provides, by the course of the strap 19 and the loop 12 via the rear of the pastern of the leg, a further support to the suspensory ligament T of the hoof, the extension of which is illustrated schematically in FIGS. 7 and 8. Upon loading of the hoof during a footfall, see FIG. 8, a strain and stretching of the loop 12 are produced, as of the strap 19, as well as of the suspensory ligament T, and more precisely in essentially parallel directions. In this way, the built-in elasticity and spring-back force of the loop 12 give an additional force that engages the rear of the pastern and primarily acts in the direction of the suspensory ligament.

The loop 12 gives in this way a back up to the suspensory ligament and constitutes in this embodiment a ligament support integrated in a hoof boot.

Preferably, for the inner boot, and particularly in respect of the loop 12/ligament support, a material is selected having toughness and ability to, upon loading, be elongated and store energy, and which, upon return from the loaded position, acts like a spring that engages the rear of the pastern and gives back up to the suspensory ligament upon raising of the leg and the joint in the pushing phase.

A ligament support 12', see FIG. 9, freestanding from the hoof boot described above is realised in the form of a monolithic or unitary, one-piece strip-shaped elastic element having an outer branching 23 and an inner branching 24, which are connected by a joint portion 25. The elastic element 23-24-25 is dimensioned to be attached in a front half of the hoof and, in the mounted position on the hoof, run via the rear of the pastern of the hoof from one of the sides or outer side of the hoof to the other or inner side of the hoof. The four strips (23, 24, 26, 27) are monolithically or unitarily formed with the central joint portion (25), and branching out from the central joint portion of the monolithic or unitary, one-piece elastic element (12').

From the joint portion 25, there start out strip parts 26 and 27 of a cuff 21', which is dimensioned to surround the leg of the horse in the area of the rear of the pastern. The cuff 21' may be arranged to be locked around the leg in an arbitrary way, e.g. by means of a VELCRO™ tape or by means of a strap lock or a corresponding locking device. As particularly seen in FIGS. 10 and 11, the ligament support, and in that connection in particular the cuff 21', may be made in such a way that the cuff in the mounted position clasps the fetlock. For the purpose, the cuff is dimensioned to extend in a vertical projection in a length w from an area underneath the fetlock to an area above the fetlock, in the mounted state of the cuff and ligament support.

The element 23-24-25 and the cuff 21' may be formed integrally, and are manufactured from a material having inherent elastic properties, such as a synthetic material, rubber, or mixtures thereof.

The inner and outer branchings 23 and 24 of the elastic ligament support may be arranged to be anchored in a conventionally formed horseshoe intended to be attached to the underside of the hoof, which horseshoe for the purpose would be formed with fastening ears protruding next to the outside and inside, respectively, of the hoof. The branchings 23, 24 of the elastic element may alternatively be anchored to the hoof by means of a rail or toecap (not shown) that is particularly formed for the purpose and arranged to be mounted on the hoof capsule.

A particularly preferred embodiment of the ligament support is shown in FIG. 10. In this embodiment, the branchings 23, 24 of the elastic element, the joint portion 25, and the cuff 21' are integrally formed in a hoof boot 100. The inner and outer branches (23, 24) are monolithically or unitarily formed into a hoof boot (100) at ends opposite said central joint portion (25). The hoof boot 100 may alternatively be in the form of an inner boot intended to, like the inner boot 10, be inserted into a sole 1 with appurtenant straps for the mounting on the hoof in a way described above. The hoof boot 100 may alternatively be in the form of a hoof boot that is fixable on the hoof by means of one or more additional straps, omitted in the drawing figure, or by agglutination.

The features being characteristic of the ligament support for hooves, as well as features belonging to preferred and meritorious embodiments of the same, are seen in more detail in attached claims.

The invention claimed is:

1. A ligament support (12') for a hoof and mountable on the hoof to back up a suspensory ligament (T), the ligament support (12') comprising:
   a monolithic or unitary, one-piece, strip-shaped elastic element (12'),
   four strips (23, 24, 26, 27) monolithically or unitarily formed with a central joint portion (25), and branching out from the central joint portion (25) of the monolithic or unitary, one-piece elastic element (12'),
   two upper strips (26, 27) of said four strips (23, 24, 26, 27) configured to surround a leg and be locked together to form a cuff (21') clasping a pastern (J),
   two lower strips (23, 24) of said four strips (23, 24, 26, 27) forming respective inner and outer branches, configured to be attached to a front half of the hoof and run, via the pastern (J), from one of an outer or inner side of the hoof to an opposite inner or outer side of the hoof, and
   the elastic element (12') made of elastic material capable of storing energy under elongation essentially in parallel with the suspensory ligament (T) between the hoof and a fetlock joint, the elastic element (12') acting as a spring in a direction of the suspensory ligament (T).

2. The ligament support (12') of claim 1, wherein said cuff (21') is dimensioned to extend, in a vertical direction, a distance (w) from an area underneath the fetlock joint to an area above the fetlock joint, and with said two upper strips (26, 27) additionally clasping the fetlock joint.

3. The ligament support (12') of claim 2, wherein said inner and outer branches (23, 24) are monolithically or unitarily formed into a hoof boot (100) at ends opposite said central joint portion (25).

4. The ligament support for hooves according to claim 1, wherein the elastic element is arranged to be detachably anchored in a hoof boot/horseshoe, and more precisely in points of attachment that are arranged for the purpose and formed in opposite sides of a hoof boot/horseshoe.

5. The ligament support for hooves according to claim 1, wherein the elastic element is fixedly anchored in opposite sides of a sole included in a hoof boot.

6. The ligament support for hooves according to claim 5, wherein the elastic element is embedded in the sole.

7. The ligament support for hooves according to claim 1, wherein the elastic element is included in an inner boot connected with a sole.

8. The ligament support for hooves according to claim 7, wherein the inner boot is co-cast with the sole in a double cast method.

9. The ligament support for hooves according to claim 1, wherein the elastic element and, where appropriate, an inner boot are manufactured from synthetic material, rubber, or mixtures thereof.

10. The ligament support for hooves according to claim 1, wherein the elastic element is dimensioned for an elongation of maximum 20-70% of an unloaded length of a strip.

\* \* \* \* \*